United States Patent
De Groot et al.

(10) Patent No.: US 10,687,927 B2
(45) Date of Patent: Jun. 23, 2020

(54) METHOD AND DEVICE TO AUTOMATICALLY DETECT CALVING

(71) Applicant: LELY PATENT N.V., Maassluis (NL)

(72) Inventors: Ester De Groot, Maassluis (NL); Xiangyu Song, Maassluis (NL); Patrick Philip Jacob Van Der Tol, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 20 days.

(21) Appl. No.: 15/752,500

(22) PCT Filed: Jul. 6, 2016

(86) PCT No.: PCT/NL2016/050484
§ 371 (c)(1),
(2) Date: Feb. 13, 2018

(87) PCT Pub. No.: WO2017/034391
PCT Pub. Date: Mar. 2, 2017

(65) Prior Publication Data
US 2018/0228587 A1     Aug. 16, 2018

(30) Foreign Application Priority Data
Aug. 21, 2015  (NL) ..................... 2015326

(51) Int. Cl.
*A61D 17/00*     (2006.01)
*G06T 7/70*      (2017.01)
(Continued)

(52) U.S. Cl.
CPC .......... *A61D 17/008* (2013.01); *A61B 5/0077* (2013.01); *A61B 5/1107* (2013.01);
(Continued)

(58) Field of Classification Search
CPC ... A61B 5/0077; A61B 5/1107; A61B 5/1123; A61B 5/1128; A61B 5/4343;
(Continued)

(56) References Cited

U.S. PATENT DOCUMENTS

| 5,412,420 A | 5/1995 | Ellis |
| 2010/0154722 A1* | 6/2010 | Van Den Berg ..... A01K 11/008 |
| | | 119/720 |

(Continued)

FOREIGN PATENT DOCUMENTS

| CA | 2 811 344 A1 | 3/2012 |
| WO | WO 2009/074153 A1 | 6/2009 |

OTHER PUBLICATIONS

International Search Report dated Sep. 29, 2016, in PCT/NL2016/050484 filed Jul. 6, 2016.

*Primary Examiner* — Leon Flores
(74) *Attorney, Agent, or Firm* — Oblon, McClelland, Maier & Neustadt, L.L.P.

(57) ABSTRACT

The invention relates to a method to automatically predict a calving moment of a cow, comprising: recording, by a three-dimensional camera system, at least one three-dimensional image of the cow, processing, by a processing device, the at least one image of the cow, wherein processing of the image comprises determining a parameter indicative of the calving moment, and predicting a calving moment of the cow on the basis of the parameter.

15 Claims, 2 Drawing Sheets

(51) Int. Cl.
*H04N 13/106* (2018.01)
*H04N 13/189* (2018.01)
*A61B 5/00* (2006.01)
*A61B 5/11* (2006.01)
*G06K 9/00* (2006.01)

(52) U.S. Cl.
CPC .......... *A61B 5/1123* (2013.01); *A61B 5/1128* (2013.01); *A61B 5/4343* (2013.01); *A61B 5/7246* (2013.01); *A61B 5/7275* (2013.01); *A61B 5/746* (2013.01); *G06T 7/70* (2017.01); *H04N 13/106* (2018.05); *H04N 13/189* (2018.05); *A61B 2503/40* (2013.01); *A61B 2576/00* (2013.01); *G06K 9/00362* (2013.01); *G06T 2207/10136* (2013.01)

(58) Field of Classification Search
CPC ..... A61B 5/7246; A61B 5/7275; A61B 5/746; H04N 13/106; H04N 13/189; A61D 17/008; G06T 7/70
See application file for complete search history.

(56) References Cited

U.S. PATENT DOCUMENTS

2011/0224581 A1* 9/2011 Cinti ................... A61B 5/1076
600/588
2011/0279650 A1 11/2011 Liao et al.
2011/0298619 A1* 12/2011 O'Hare ............... A01K 11/008
340/573.1
2017/0325426 A1* 11/2017 Brosh ................. A01K 11/008

* cited by examiner

METHOD AND DEVICE TO AUTOMATICALLY DETECT CALVING

BACKGROUND OF THE INVENTION

Field of the Invention

The invention relates to a method and device to automatically detect calving, using three dimensional images of the animal.

Description of the Related Art

In current practice, farmers lack the time to constantly monitor a cow that is about to deliver a calf. The current method of manually monitoring the cow is labour intensive, time consuming and prone to errors.

Generally, the birth of a calf comprises three phases, the preparation phase, the delivery phase and the post-delivery phase.

In the preparation phase, the cow prepares for the delivery of a calf. The cervix, vagina and vulva all dilate and the cervical mucous plug is released. All these changes are to facilitate the passage of the calf. The start of the second stage of labor, the delivery phase, is signalled by the appearance of the water bag. The preparation phase may for example last up to 72 hours.

In the delivery phase, the expulsion of the calf through the birth canal takes place. Duration of this stage may last from one-half hour in the cow to two or three hours in a first-calf heifer. The beginning of the delivery phase in which actual delivery of the calf takes place is also indicated as the calving moment.

The post-delivery phase comprises expulsion of the fetal membranes, i.e. placenta, and involution of the uterus. The placenta is usually expelled within a few hours of birth but complete involution of the uterus takes up to 40 days after calving.

BRIEF SUMMARY OF THE INVENTION

It is an aim of the present invention to provide a method and device to automatically monitor a cow in labor and predict the calving moment of the cow.

The present invention provides a method according to claim 1.

The method of the invention proposes the use of three dimensional images of a pregnant cow to deduct at least one parameter indicative for a calving moment. The prediction of the calving moment can be an predicted time for start of the delivery of the calf or can be a prediction of a period in which the calving is expected. In an alternative embodiment, the prediction may be a likelihood that the delivery phase will start within a certain period, for example the chance of start delivery within the next ten minutes is 90%. Any other prediction for the start of the delivery phase may also be used.

A number of different parameters may be used to predict the calving moment. These parameters may be selected from the group consisting of:
  a body contraction parameter representative for the body contraction of the cow;
  an orientation parameter representative for the orientation of the cow;
  a pin line length parameter representative for a distance between the two pin bone points;
  a laying down parameter representative for the laying down frequency of the cow; and
  a tail movement parameter representative for tail movements of the cow.

Body contraction can be used as a suitable indicator to predict the calving moment. At the same time the body contraction of a cow can be reliable determined on the basis of three dimensional images.

Body contraction can be determined by monitoring a body contraction parameter of the body of the cow. For, example the body contraction can be determined by the following two steps. In a first step, a center, e.g. a volume center or a mass center, of the body is determined. In a second step, distances between the center and image pixels arranged at the outer surface of the body are used to calculate a body contraction parameter.

The body contraction parameter may for example be the sum or an average of these distances. The number and location of image pixels arranged at the outer surface of the body of the cow are selected such that they are representative for the outer surface of the body of the cow. Preferably, all image pixels at the outer surface are used to calculate the body contraction parameter.

The change in the orientation of the cow in labor is also a good indicator to predict the calving moment of a cow. During the preparation phase cows in labor tend to walk around and as a result show a substantial change in the orientation of the cow. When this change in orientation of the cow substantially stops, it is likely that the delivery phase starts. As a result, the calving moment may be predicted on the basis of this change in orientation. Orientation of a cow and any change therein can reliably be determined by a 3D camera system.

The pin line length is another indicator for the prediction of a calving moment. The position of the pins, also called the pin bone points, of the cow can reliable be determined on the basis of three dimensional images. The distance between the two pins, herein referred to as pin line length, will normally remain constant during a period of a day. However, for the delivery of a calf Relaxin, a glycoprotein, is produced for softening of connective tissue in the cervix and promoting elasticity of the pelvic ligaments, allowing easier passage of the calf. This softening results in that a distance between the pin bone points, i.e. the pin line length, will increase. By monitoring the pin line length the calving moment can be predicted.

Other parameters that can be used to predict a calving moment of a cow may be a laying down parameter representative for the laying down frequency of the cow and a tail movement parameter representative for tail movements of the cow.

The frequency with which the cow lays down and stands up again will usually increase in the period before the actual delivery of the calf. This so-called laying down frequency can be monitored using three-dimensional images recorded by the three-dimensional camera system.

Similarly, the tail movements of the cow in the period before the actual delivery of the calf normally will increase both in frequency as amplitude. These tail movements can also be monitored using three-dimensional images recorded by the three-dimensional camera system.

In an embodiment, the method comprises:
  recording, by the three-dimensional camera system, multiple three-dimensional images of the cow,
  processing, by the processing device, the images, wherein processing of the multiple images comprises:

determining a development of the parameter in the course of time, comparing the parameter with reference data, and predicting the calving moment of the cow on the basis of the comparison.

The method of the invention comprises a prediction of a calving moment of a cow using one or more parameters determined on the basis of three-dimensional camera images. Some parameters can be monitored over the course of time and compared with reference data.

In an embodiment, the method comprises providing a warning signal when a predicted calving moment is established and/or calving is started. The advantage of the method according to the invention is that the farmer does not have to continuously monitor a cow in labour. However, when the actual delivery phase has started the farmer can be warned by a warning signal. The farmer can decide whether he wants to be present during the actual delivery of the calf. Traditionally the farmer would like to be present during the calving moment to assist, when needed, the cow during delivery of the calf.

However, the present method may also comprise the step of monitoring actual delivery of the calf using three-dimensional images recorded by the three-dimensional camera system. In such method, the method may further comprise the step of providing a warning signal when the time period of actual delivery is longer than a predetermined maximum calving time.

Normally, the actual delivery of a calf will take a period of maximally one half hour. If at the end of this period the calf has not been delivered, this may indicate that there are difficulties in the delivery of the calf. Therefore, it is desirable to inform a farmer with a warning signal that the period has lapsed without complete delivery of a calf.

The warning signal may be any signal such as a light or audible signal, but is preferably a communication signal that can be sent to a mobile telephone or other mobile device that can be carried by the farmer.

In an embodiment, a combination of two or more parameters, preferably selected from the group consisting of a body contraction parameter representative for the body contraction of the cow an orientation parameter representative for the orientation of the cow, a pin line length parameter representative for a distance between the two pin bone points, a laying down parameter representative for the laying down frequency of the cow; and a tail movement parameter representative for tail movements of the cow, are used to predict the calving moment.

Although each of the parameters described above individually may be used to predict a calving moment of a cow, it has been found that a combination of two or more parameters substantially increases the accuracy of the prediction of the calving moment.

For instance, a combination of the body contraction parameter and the orientation parameter may be used to predict the calving moment. The combination of the two or more parameters may comprise any suitable mathematical combination, such as a ratio between two parameters, a sum or multiplication of two parameters, or any combination thereof in order to calculate a single parameter to predict the calving moment. Constants may be used to weigh the parameters with respect to each other. As an example the parameter may be calculated as:

$$P=K_C \cdot P_C + K_O \cdot P_O,$$

wherein P is the parameter on the basis of which a calving moment may be predicted, $K_C$ a weighing constant for the body contraction parameter, $P_C$ the body contraction parameter, $K_O$ a weighing constant for the orientation parameter, and $P_O$ the orientation parameter.

In an embodiment the images are processed real time when they are recorded, or near real time. This means that images are processed at the time that they are recorded or at least without significant lag time between recording and processing of the image. Such real time processing is beneficial to the predictive capacity of the method. In this sense real time means that when images are recorded at certain frame rate these images can be processed at the same frame rate or faster. Real time processing of the images may also mean that the processing rate is at least as fast as the sample rate, in case not each recorded image is processed but a sample of the recorded images is taken at a certain sample rate. Typically such a sample rate will be lower than the image recording rate. Near real time is similar to real time but allows for a lag time between the recording and processing. The time delay of Near Real Time processing is introduced by e.g. data transfer of the recorded image in order for it to be processed. The invention further provides a device to predict a calving moment of a cow, comprising:

a three-dimensional camera system configured to record at least one three-dimensional image of the cow, a processing device configured to process the image of the cow, said processing comprises the steps of:

determining at least one parameter indicative of the calving moment, and predicting a calving moment of the cow on the basis of the parameter.

In an embodiment, the at least one parameter is selected from the group consisting of:

a body contraction parameter representative for the body contraction of the cow;

an orientation parameter representative for the orientation of the cow;

a pin line length parameter representative for a distance between the two pin bone points;

a laying down parameter representative for the laying down frequency of the cow; and a tail movement parameter representative for tail movements of the cow.

BRIEF DESCRIPTION OF THE SEVERAL VIEWS OF THE DRAWINGS

Embodiments of a method and arrangement according to the invention will now be described in further detail, by way of example only, with reference to the accompanying drawings, in which.

DETAILED DESCRIPTION OF THE INVENTION

Figure 1:
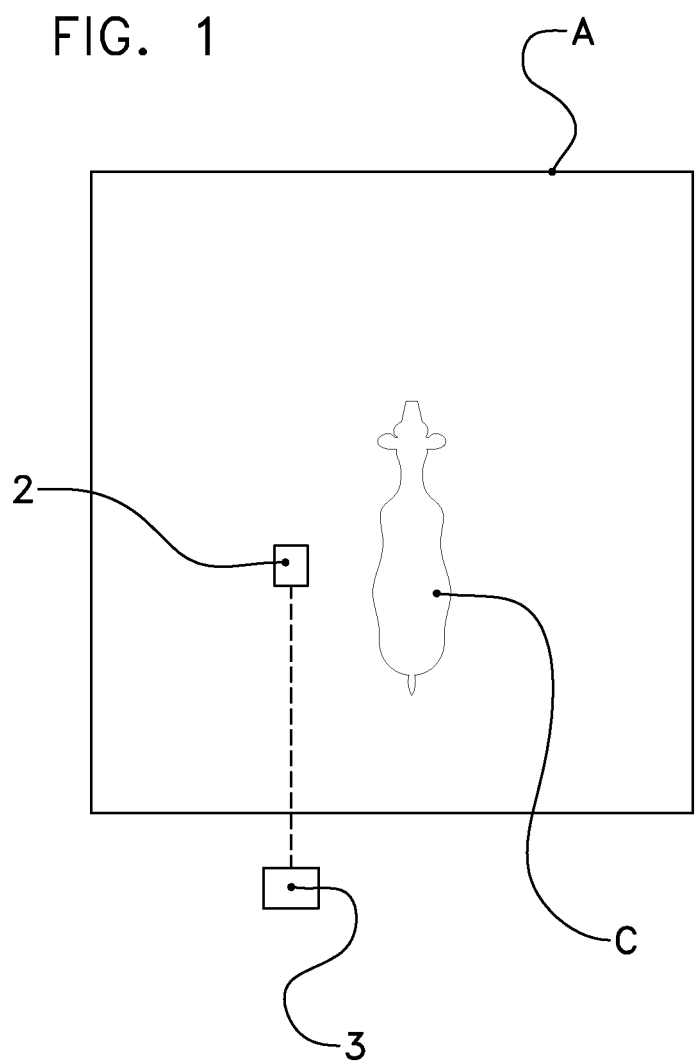
FIG. 1 shows a top view of a combination of a fenced area and a monitoring device.

FIG. 1 shows a side view of a fenced area A in which a cow C is held in the final phase of the pregnancy of the cow C. A monitoring device is provided to monitor a cow C present in the area A, in particular to predict the calving moment of the cow C. The monitoring device comprises a three-dimensional camera system 2 and a processing device 3 connected to the camera system 2.

The three-dimensional camera system 2 is configured and arranged to record three-dimensional images of a cow present in the area A. The three-dimensional camera system 2 may comprise any suitable three dimensional camera such as an ASUS Xtion Pro Live (depth) having a resolution 640*480 and taking images at a rate of 30 frames per second.

The camera system 2 may be provided for example at least 2 m above floor level.

The camera system 2 is configured to record three-dimensional images of the cow C, whereby the cow C may be in any position within the area A. To cover the whole area A, the camera system 2 may be movable to different positions above the area A. In other embodiments, multiple camera systems 2 may be provided that together cover the area A.

The processing device 3 is configured to process the image. The processing device 3 may be any suitable device for processing the three dimensional images taken by the three-dimensional camera system 2, and may be a separate device or integrated in the three-dimensional camera system 2. The processing device 3 may also be integrated in a central processing device, for example a central computer device configured to monitor a number of cows, such as a herd management system, and/or configured to monitor and control one or more automatic feeding devices. The processing device may be a real time image processor capable at least matching the rate in which the images are recorded. E.g. when the camera records images at the rate of 30 frames per second, the real time image processer is capable of processing these recorded images at the same rate or faster. In which case the processer when having finished processing an image may have to wait for the next image to be recorded. In some cases it is possible not to process every recorded image, but the sample images at a sample rate. For example when the camera may record 100 images per second, these images may be sampled at a lower rate such as e.g. 25 frames per second. In that case the real time image processer need only to match the sample rate.

Processing of the image involves a number of steps to process the image from coarse image data as obtained by the camera system 2 to a three-dimensional surface representation of at least a part of the cow C.

As a first step, coarse image data obtained by the three-dimensional camera system 2, usually comprising distance data from camera to cow may be transformed to data in an orthogonal coordinate system.

Then, noise and background in the image may be removed. Noise can be removed by known filtering techniques. Furthermore, it is known that some fixed objects such as fences may be present in the image. It is advantageous to filter out this background as this may influence the results in later steps of the method.

As a result of the first image processing steps the image points may have a coarse distribution in some areas of the image and/or have a very fine distribution in other areas of the image. For further processing of the image, it may be desirable to have a relative even and fine distribution of image points over the image. To obtain such even and fine distribution of image point over the whole images new point may be defined by interpolation between surrounding image points. In this way, an even distribution with an accuracy of for example 2 to 5 mm, such as 3 mm may be obtained. It may be possible to recalculate the points to an even distributed matrix of image points having rows and columns with a constant pitch of for example 3 mm.

Finally, the image may be centralized at a predetermined central image axis. To properly define relevant surface parts of the image, it is desirable that the image is arranged at a suitable angle with respect to the image axes, i.e. the axes of the coordinate system in which the image is defined. In particular, it is desirable to align the spine line, i.e. the longitudinal axis of the spinal ridge, with a central image axis of the coordinate system in which the image is defined.

This centralizing step can be performed by determining, in the image, a spine line of the cow, and translating and rotating the image to align the spine line with the central image axis. Since the coarse position of the cow in the image is known, the spine line can be found by finding the highest points of the image in an area of the image where the spine is expected, and defining the spine line as a straight line through the highest points in this area.

The area can for example be defined as an area extending equally at opposite sides of the central image axis, but can also be determined on the basis of coarse image data, for example by calculating an area having a relative large number of high points in the image.

In an embodiment, the spine line can be coarsely estimated by summing all points in length direction of the cow, resulting in a height profile in width direction of the cow, and defining a coarse spine line at the highest point of the height profile. Subsequently, the spine line can be determined more accurately by finding the highest point in an area extending at both sides of the coarse spine line.

Figure 2:
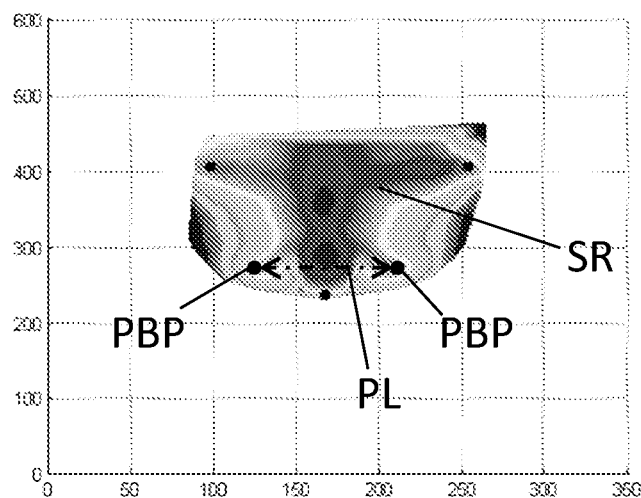
FIG. 2 shows a surface representation of a top surface of a part of a cow.

FIG. 2 shows a surface representation SR of a top part of an outer surface of the cow after the above discussed processing steps.

The processing device 3 is further configured to determine on the basis of the one or more images recorded by the camera system 2 at least one parameter indicative of the calving moment of the cow. Typically the three dimensional surface representations based on the images are used to determine one or more parameters that are used to predict a calving moment of Parameters that can be determined and monitored by using three-dimensional images for example include a body contraction parameter representative for the body contraction of the cow, an orientation parameter representative for the orientation of the cow, a pin line length parameter representative for a distance between the two pin bone points, a laying down parameter representative for the laying down frequency of the cow, and a tail movement parameter representative for tail movements of the cow.

During the delivery phase body contractions occur. These body contractions can be detected by comparing subsequent surface representations of the body of the cow. From this comparison, it can be determined whether the body volume changes, i.e. whether body contractions occur, and the intensity of these body contractions.

When the delivery phase approaches, the body contractions will increase in frequency and/or intensity. As a result, the body contractions can be used to predict the calving moment of the cow.

In order to properly detect the body contractions, it is advantageous to use an image frequency with which three-dimensional images are recorded that is larger than the frequency with which the body contractions occur.

Figure 3:
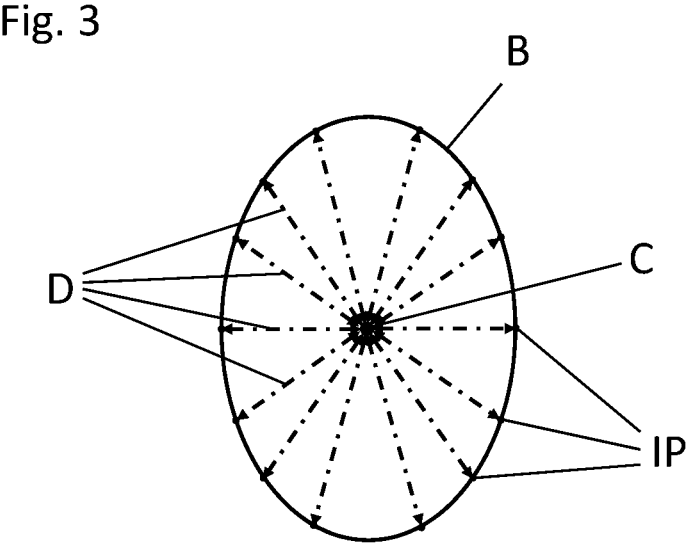
FIG. 3 shows schematically a method to calculate the body contraction parameter.

The body contraction can be determined by the following two steps, as schematically shown in FIG. 3. In a first step, a center C of the body B, e.g. a mass center or volume center, is determined. In a second step, the sum of distances D between the center C and a relatively large number of image pixels IP arranged at the outer surface of the body B is determined as the body contraction parameter. This sum of distances is representative for the volume of the body, and can thus be used to calculate the intensity and/or frequency of body contractions of the cow.

Any other variable dependent on the distances between the center and image pixels arranged at the outer surface of the body, such as average distance, may also be used. A relatively large number of image pixels at the outer surface of the body of the cow is selected such that the image pixels are representative for the outer surface of the body of the cow. Preferably, all image pixels at the outer surface are used to calculate the body contraction parameter. In this respect, it is remarked that FIG. 3 only shows image pixels IP in a two-dimensional plane. In practice, the use of three-dimensional images allows to calculate distances D between the outer surface of the body B and the center C in three dimensions.

Another parameter that can be used to predict the calving moment of a cow is the orientation of the cow.

The change in orientation of the cow will usually show a gradual increase in the phase before delivery of a calf, but will become very low shortly before the delivery phase of the calf. By monitoring the orientation of the cow this gradual increase and sudden stop of the change in orientation can be detected and the calving moment of the cow can be predicted.

The orientation of a cow can for example be determined by determining a positional relationship between the head and body of a cow. This can be done by recognizing the head position and the body position of the cow and connecting the middle points of the head position and the body position. Alternatively, the orientation can be determined by determination of the spine line of the cow in a surface representation of the back of the cow. The spine line can relatively accurately be detected in three-dimensional images taken from above.

A further parameter that can be used to predict the calving moment of the cow is the distance between the pin bone points, i.e. the pin line length. The distance between the pin bone points normally does not change during a relatively short period, such as a day.

However, during the preparation phase of a delivery of a calf, the cow will produce Relaxin, a glycoprotein, for softening of connective tissue in the cervix and promoting elasticity of the pelvic ligaments. This will result in a larger distance between the pin bone points.

The position of the pin bone points can accurately be determined in a three dimensional surface representation of a cow. FIG. 2 shows the location of the pin bone points PBP in the surface representation SR. The distance between the pin bone points PBP is the pin line length PL. Thus, also the distance between these pin bone points PBP can accurately be determined. By monitoring the pin line length PL, the increase of this pin line length PL can be detected on the basis of the three-dimensional surface representations based on the three-dimensional images recorded by the camera system 2.

The laying down frequency of the cow can also be used to predict the calving moment of the cow. When a cow is close to the delivery phase, the frequency with which the cow lays down and stands up increases.

The three dimensional images can be used to determine a height of the cow, for example the maximum height of the cow or the height of a characteristic point or area of the cow, such as the height of the hip bones.

On the basis of the determined height, it can be determined whether the cow is standing or laying on the floor.

Yet another parameter that can be used to predict the calving moment of a cow is the tail movement parameter representative for tail movements of the cow. When the delivery phase of a cow approaches, the number and amplitude of tail movements will increase. The tail movements may be determined on the basis of three-dimensional images recorded by the camera system 2.

Once the parameter is determined, the parameter can be used to predict the start of the actual delivery phase of the cow. This prediction can for example be a predicted time for start of the delivery of the calf or a prediction of a period in which the calving is expected. As, the prediction may be a likelihood that the delivery phase will start within a certain period, for example the chance of start delivery within the next ten minutes is 90%. Any other prediction for the start of the delivery phase may also be used.

In practice, two or more parameters may be used in combination to accurately predict the calving moment. For example, a body contraction parameter, representative for a intensity and/or frequency of body contractions and an orientation parameter representative for the change in orientation may both be monitored.

When both parameters predict that a calving moment will occur in the next 10 minutes, it will be assumed that the calving moment will take place in the next 10 minutes.

The two or more parameters may also be combined in a single parameter to predict the calving moment. The combination of the two or more parameters may comprise any suitable mathematical combination, such as a ratio between two parameters, a sum or multiplication of two parameters, or any combination thereof.

Constants may also be used to weigh the parameters with respect to each other. As an example the parameter may be calculated as:

$$P=K_C \cdot P_C + K_O \cdot P_O,$$

wherein P is the parameter on the basis of which a calving moment may be predicted, $K_C$ a weighing constant for the body contraction parameter, $P_C$ the body contraction parameter, $K_O$ a weighing constant for the orientation parameter, and $P_O$ the orientation parameter.

When the prediction that the actual delivery will take place in the next 10 minutes a warning signal may be sent to the farmer, for example a digital communication signal to a mobile device, such as mobile telephone or tablet, to warn the farmer that actual delivery will shortly begin.

On the basis of the warning signal, the farmer can decide whether he will go to the area A to assist in delivery of the calf, or wait for any further communication signals with respect to the delivery of the calf.

Also other signals may be sent to a mobile device of the farmer. For example, the development of the parameters may regularly be sent to the farmer to provide insight in this development of the parameters in the course of time.

The camera system 2 and processing device 3 may also be used to monitor the delivery phase of the cow. For example, on the basis of the three-dimensional images the birth of the calf may be followed, and when needed a warning signal may be sent to the farmer to warn when the cow needs to be assisted. Such warning signal may for example be emitted, when the time duration of the actual delivery of the calf takes longer than a predetermined time, for example more than 30 minutes.

The invention claimed is:

1. A method to automatically predict a calving moment of a pregnant cow, comprising: recording, by a three-dimensional camera system, at least one three-dimensional image of the cow; and processing, by processing circuitry, the at least one image of the cow, wherein processing of the image comprises: determining at least one a first parameter and a second parameter indicative of the calving moment, and predicting on the basis of the first parameter and the second parameter a calving moment of the cow, wherein the first parameter is an orientation parameter representative of an orientation of the cow, wherein a second parameter is a body contraction parameter representative of body contraction of the cow, and wherein the predicting of the calving moment of the cow is performed based on a weighed combination of the first and second parameter, wherein the weighted combination applies a weight that is more than 0 and less than 1.

2. The method of claim 1, wherein the method comprises:
recording, by the three-dimensional camera system, multiple three-dimensional images of the cow,
processing, by the processing circuitry, the images, wherein processing of the multiple images comprises:
determining a development of the parameter in the course of time,
comparing the parameter with reference data, and
predicting the calving moment of the cow on the basis of the comparison.

3. The method of claim 1, wherein predicting a calving moment comprises predicting whether the calving moment will occur within the next 1 to 10 minutes.

4. The method of claim 1, wherein the method comprises providing a warning signal when a predicted calving moment is established and/or calving is started.

5. The method of claim 1, wherein the method comprises monitoring actual delivery of the calf.

6. The method of claim 5, wherein the method comprises
providing a warning signal when the time period of actual delivery of the calf is longer than a predetermined maximum calving time.

7. The method of claim 1, wherein predicting a calving moment of the cow is based on the combination of two or more parameters.

8. The method of claim 7, wherein the predicting is further performed on the basis of at least one additional parameter selected from a group consisting of: a pin line length parameter representative for a distance between the two pin bone points; a laying down parameter representative for the laying down frequency of the cow; and a tail movement parameter representative for tail movements of the cow.

9. The method of claim wherein the processing of the at least one image takes place real time or near real time.

10. A device to predict a calving moment of a cow, comprising: a three-dimensional camera system configured to record at least one three-dimensional image of the cow, processing circuitry configured to process the at least one image of the cow, said processing comprises: determining at least one a first parameter and a second parameter indicative of the calving moment, and predicting a calving moment of the cow on the basis of the first parameter and the second parameter, wherein the first parameter is an orientation parameter representative of an orientation of the cow, wherein a second parameter is a body contraction parameter representative of body contraction of the cow, and wherein the predicting of the calving moment of the cow is performed based on a weighed combination of the first and second parameter, wherein the weighted combination applies a weight that is more than 0 and less than 1.

11. The method of claim 7, wherein the predicting is further performed on the basis of at least one additional parameter selected from a group consisting of: a pin line length parameter representative for a distance between the two pin bone points; a laying down parameter representative for the laying down frequency of the cow; and a tail movement parameter representative for tail movements of the cow.

12. The device of claim 10, wherein the device comprises a warning device to provide a warning signal when a predicted calving moment is established and/or calving is started.

13. The device of claim 10, wherein the process comprises monitoring actual delivery of the calf.

14. The device of claim 10, wherein the processing comprises
recording, by the three-dimensional camera system, multiple three-dimensional images of the cow,
processing, by the processing device, the multiple images, wherein processing of the multiple images comprises:
determining a development of the parameter in the course of time,
comparing the parameter with reference data, and
predicting the calving moment of the cow on the basis of the comparison.

15. The device of claim 10. wherein predicting a calving moment comprises predicting whether the calving moment will occur within the next 1 to 10 minutes.

* * * * *